US010226442B2

United States Patent
Tsai et al.

(10) Patent No.: US 10,226,442 B2
(45) Date of Patent: Mar. 12, 2019

(54) LITHIUM SALTS OF N-SUBSTITUTED GLYCINE COMPOUNDS AND USES THEREOF

(71) Applicant: SyneuRx International (Taiwan) Corp., New Taipei (TW)

(72) Inventors: Guochuan Emil Tsai, Pasadena, CA (US); Ching-Hsun Huang, Taipei (TW); Han-Yi Hsieh, New Taipei (TW); Jing-Jia Huang, New Taipei (TW); Ching-Cheng Wang, New Taipei (TW)

(73) Assignee: SyneuRx International (Taiwan) Corp., New Taipei (TW)

( * ) Notice: Subject to any disclaimer, the term of this patent is extended or adjusted under 35 U.S.C. 154(b) by 0 days.

(21) Appl. No.: 15/646,034

(22) Filed: Jul. 10, 2017

(65) Prior Publication Data

US 2019/0008813 A1  Jan. 10, 2019

(51) Int. Cl.
| | |
|---|---|
| *A23L 33/00* | (2016.01) |
| *A23L 33/16* | (2016.01) |
| *A61K 31/12* | (2006.01) |
| *A61K 31/40* | (2006.01) |
| *A61K 45/06* | (2006.01) |
| *A61K 31/198* | (2006.01) |
| *A61K 31/382* | (2006.01) |
| *A61K 31/407* | (2006.01) |
| *A61K 31/496* | (2006.01) |
| *A61K 31/519* | (2006.01) |
| *A61K 31/554* | (2006.01) |
| *A61K 31/4439* | (2006.01) |
| *A61K 31/5415* | (2006.01) |
| *A61K 31/5513* | (2006.01) |

(52) U.S. Cl.
CPC ............ *A61K 31/198* (2013.01); *A23L 33/16* (2016.08); *A23L 33/30* (2016.08); *A61K 31/12* (2013.01); *A61K 31/382* (2013.01); *A61K 31/40* (2013.01); *A61K 31/407* (2013.01); *A61K 31/4439* (2013.01); *A61K 31/496* (2013.01); *A61K 31/519* (2013.01); *A61K 31/5415* (2013.01); *A61K 31/554* (2013.01); *A61K 31/5513* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2,796,349 A | 6/1957 | Colten et al. | |
| 4,540,582 A | 9/1985 | Seiler et al. | |
| 6,228,875 B1 * | 5/2001 | Tsai | A61K 31/198 514/380 |
| 7,704,978 B2 | 4/2010 | Tsai et al. | |
| 9,415,030 B2 * | 8/2016 | Cleveland | A61K 31/198 |
| 2012/0041066 A1 | 2/2012 | Lombard | |

FOREIGN PATENT DOCUMENTS

| | | | | |
|---|---|---|---|---|
| WO | WO-2009018368 A1 * | 2/2009 | | A61K 45/06 |
| WO | WO 2016/004363 A2 | 1/2016 | | |

OTHER PUBLICATIONS

Brown, Bioorganic & Medicinal Chemistry Letters, 11, 2001 (Year: 2001).*
O'Donnell, Neurosci Biobehav Rev, 31, 6, 2007 (Year: 2007).*
Fleck et al., Two forms of sarcosine sarcosinium hydrogen L-tartrate. J. Mol Structure. 2013;1045: 95-103.
Losev et al., Polymorphic transformations in glycine co-crystals at low temperature and high pressure: two new examples as a follow-up to a glycine-glutaric acid study. CrystEngComm. 2016; 18: 5869-75.
Losev et al., The effect of carboxylic acids on glycine polymorphism, salt and co-crystal formation. A comparison of different crystallization techniques. New J Chem. 2013;37:1973-81.
Tsai et al., Strategies to enhance N-methyl-D-aspartate receptor-mediated neurotransmission in schizophrenia, a critical review and meta-analysis. Curr Pharm Des. 2010;16(5):522-37.
Van Holst et al., Kinetic study of CO2 with various amino acid salts in aqueous solution. Chem Eng Sci. Jan. 2009;64(1):59-68.
Pubchem-CID: 91872689. dated Sep. 21, 2015. 1-11.

* cited by examiner

*Primary Examiner* — Susan T Tran
*Assistant Examiner* — William Craigo
(74) *Attorney, Agent, or Firm* — Wolf, Greenfield & Sacks, P.C.

(57) ABSTRACT

The present invention relates to a composition comprising a lithium salt of an N-substituted glycine compound and a carrier, wherein the lithium salt of the N-substituted glycine compound is of Formula (I):

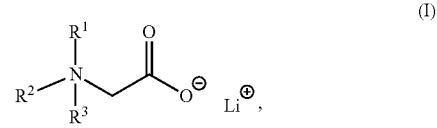

in which $R^1$, $R^2$, and $R^3$ each are independently hydrogen, alkyl, alkenyl, alkynyl, aralkyl, carbocyclyl, aryl, or heteroaryl, or one of $R^1$, $R^2$, and $R^3$ is absent. Also provided in the present invention is a method of mitigating at least one symptom of a neuropsychiatric disorder, comprising administering to a subject in need thereof the lithium salt of an N-substituted glycine compound of Formula (I).

22 Claims, 4 Drawing Sheets

LITHIUM SALTS OF N-SUBSTITUTED GLYCINE COMPOUNDS AND USES THEREOF

BACKGROUND OF THE INVENTION

Neuropsychiatric disorders, such as schizophrenia, affect the behavior of patients and impair the cognition and learning ability of the patients. These disorders also result in dysfunction of the cognitive process, such as delusions, hallucinations, and extensive withdrawal of the patient's interests from other people. Neuropsychiatric disorders, which are characterized by a deficit in neurotransmission via the N-methyl-D-aspartate (NMDA) receptor, can be alleviated by compounds that act as a glycine uptake inhibitor, such as N-methylglycine.

N-methylglycine is an amino acid naturally produced in the metabolism of choline. It has been applied to the treatment of major depression (Huang et al., Biological Psychiatry, 2013 Nov. 15; 74(10):734-41) and schizophrenia. It has been confirmed that N-methylglycine improves negative and cognitive symptoms in schizophrenia (Amiaz et al., *Isr J Psychiatry Relat Sci.* 2015; 52(1):12-5; Strzelecki et al., *Neurosci Lett.* 2015 Oct. 8; 606:7-12).

SUMMARY OF THE INVENTION

The present invention is based on the unexpected finding that lithium salts of N-substituted glycine compounds have greater effects for mitigating symptoms of neuropsychiatric disorder, for example, positive symptoms of schizophrenia and negative symptoms of schizophrenia and cognitive dysfunctions.

Accordingly, provided herein are lithium salts of an N-substituted glycine compound and uses thereof for mitigating at least one symptom of a neuropsychiatric disorder.

In one aspect, the present invention provides a composition comprising a lithium salt of an N-substituted glycine compound and a carrier, wherein the lithium salt of the N-substituted glycine compound is of Formula (I), (I)

in which $R^1$, $R^2$, and $R^3$ each are independently hydrogen, alkyl, alkenyl, alkynyl, aralkyl, carbocyclyl, aryl, or heteroaryl, or one of $R^1$, $R^2$, and $R^3$ is absent.

In some embodiments, the lithium salt of the N-substituted glycine compound is of Formula (I-A):

(I-A)

in which $R^1$, $R^2$, and $R^3$ each are independently hydrogen, alkyl, alkenyl, alkynyl, aralkyl, carbocyclyl, aryl, or heteroaryl.

In some embodiments, the lithium salt of the N-substituted glycine compound is of Formula (I-B):

(I-B)

in which $R^1$ and $R^2$ each are independently hydrogen, alkyl, alkenyl, alkynyl, aralkyl, carbocyclyl, aryl, or heteroaryl.

In any of the lithium salt of the N-substituted glycine compounds described herein, at least two of $R^1$, $R^2$, and $R^3$ each are independently hydrogen or alkyl. In some embodiments, alkyl is $C_{1-3}$ alkyl, for example, methyl.

In some embodiments, $R^1$ and $R^2$ are each methyl and $R^3$ is absent in the lithium salt of the N-substituted glycine compounds described herein. In other embodiments, $R^1$ is methyl, $R^2$ is hydrogen, and $R^3$ is absent.

In some embodiments, the composition described herein can be a pharmaceutical composition, a nutraceutical composition, a health food, or a medical food.

In another aspect, the present disclosure provides a method of mitigating a symptom of a neuropsychiatric disorder, comprising administering to a subject in need thereof an effective amount of any of the lithium salt of an N-substituted glycine compound or a composition comprising such.

The details of one or more embodiments of the disclosure are set forth herein. Other features, objects, and advantages of the disclosure will be apparent from the Detailed Description, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

When a range of values is listed, it is intended to encompass each value and sub-range within the range. For example, "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl (C4) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F, or —OH). In certain embodiments, the alkyl group is an unsubstituted $C_{1-10}$ alkyl (such as unsubstituted $C_{1-6}$ alkyl or $C_{1-3}$ alkyl, e.g., —$CH_3$). In certain embodiments, the alkyl group is a substituted $C_{1-10}$ alkyl (such as substituted $C_{1-6}$ alkyl or $C_{1-3}$ alkyl, e.g., —$CF_3$ or $CH_2OH$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=$CHCH_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl. Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

As used herein, the term "salt" refers to any and all salts, and encompasses pharmaceutically acceptable salts.

The term "crystalline" or "crystalline form" refers to a solid form substantially exhibiting three-dimensional order. In certain embodiments, a crystalline form of a solid is a solid form that is substantially not amorphous. In certain embodiments, the X-ray powder diffraction (XRPD) pattern of a crystalline form includes one or more sharply defined peaks.

The term "amorphous" or "amorphous form" refers to a form of a solid ("solid form"), the form substantially lacking three-dimensional order. In certain embodiments, an amorphous form of a solid is a solid form that is substantially not crystalline. In certain embodiments, the X-ray powder diffraction (XRPD) pattern of an amorphous form includes a wide scattering band with a peak at $2\theta$ of, e.g., between 20 and 70°, inclusive, using CuK$\alpha$ radiation. In certain embodiments, the XRPD pattern of an amorphous form further includes one or more peaks attributed to crystalline structures. In certain embodiments, the maximum intensity of any one of the one or more peaks attributed to crystalline structures observed at a $2\theta$ of between 20 and 70°, inclusive, is not more than 300-fold, not more than 100-fold, not more than 30-fold, not more than 10-fold, or not more than 3-fold of the maximum intensity of the wide scattering band. In certain embodiments, the XRPD pattern of an amorphous form includes no peaks attributed to crystalline structures.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. A "patient" refers to a human subject in need of treatment of a disease.

The terms "administer," "administering," or "administration" refers to implanting, absorbing, ingesting, injecting, inhaling, or otherwise introducing a lithium salt of an N-substituted glycine compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen) to delay or prevent disease occurrence. Treatment may also be continued after symptoms have resolved, for example, to delay or prevent recurrence.

The terms "mitigation," "mitigate," and "mitigating" refer to reducing the severity or extent of one or more symptoms of a disease or condition described herein.

The terms "condition," "disease," and "disorder" are used interchangeably.

An "effective amount" of the lithium salt of an N-substituted glycine compound described herein refers to an amount sufficient to elicit the desired biological response, i.e., treating the condition. As will be appreciated by those of ordinary skill in this art, the effective amount of the lithium salt of an N-substituted glycine compound described herein may vary depending on such factors as the desired biological endpoint, the pharmacokinetics of the lithium salt of an N-substituted glycine compound, the condition being treated, the mode of administration, and the age and health of the subject. In certain embodiments, an effective amount is a therapeutically effective amount. In certain embodiments, an effective amount is a prophylactic effective amount. In certain embodiments, an effective amount is the amount of a lithium salt of an N-substituted glycine compound described herein in a single dose. In certain embodiments, an effective amount is the combined amounts of a lithium salt of an N-substituted glycine compound described herein in multiple doses.

A "therapeutically effective amount" of a lithium salt of an N-substituted glycine compound described herein is an amount sufficient to provide a therapeutic benefit in the treatment of a condition or to delay or minimize one or more symptoms associated with the condition. A therapeutically effective amount of a lithium salt of an N-substituted glycine compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a lithium salt of an N-substituted glycine compound described herein is an amount sufficient to prevent a condition, or one or more symptoms associated with the condition or prevent its recurrence. A prophylactically effective amount of a lithium salt of an N-substituted glycine compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "neuropsychiatric disorder," including either neurological diseases or psychiatric disorders or CNS (central nervous system) disorders, or refers to a disorder that involves either psychiatric symptoms or syndromes caused by organic brain disorders. The main characteristics of neuropsychiatric symptoms include occurrence of the various psychiatric symptoms, cognitive impairment, neurological symptoms or the possibility of early cerebral development symptoms. For example, the neuropsychiatric disorder can include, but is not limited to, schizophrenia, psychotic disorders, major depressive disorder, Alzheimer's disease, dementia, frontotemporal dementia, mild cognitive impairment, benign forgetfulness, closed head injury, an autistic spectrum disorder, Asperger's disorder, Fragile X syndrome, attention deficit hyperactivity disorders, combined attention-deficit hyperactivity disorder and tic disorder, obsessive compulsive disorder, tic disorders, Tourette's syndrome, childhood learning disorders, premenstrual syndrome, depression, suicidal ideation and/or behavior, bipolar disorders, anxiety disorders, panic disorders, post-traumatic stress disorder, chronic pain, eating disorders, addiction disorders, personality disorders, Parkinson's disorder, Huntington's disorder, amyotrophic lateral sclerosis, nocturnal enuresis, stroke, Duchenne muscular dystrophy, blepharospasm and non-epileptic seizures.

As used herein, the term "neuropsychiatric disorder with hyperactivity symptoms" refers to any neuropsychiatric disorder that exhibits hyperactivity as a disease symptom, which can be determined by routine medical procedures. Examples include, but are not limited to, schizophrenia, bipolar disorder, attention-deficit hyperactivity disorder, obsessive compulsive disorder, Tourette's syndrome, autism spectrum disorders, Fragile X syndrome, Parkinson's disease, dementia with Lewy bodies, and senile dementia.

As used herein, the term "neuropsychiatric disorder having sensorimotor deficit" refers to any neuropsychiatric disorder associated with impaired sensorimotor activity, which can be determined by routine medical procedures. Examples include, but are not limited to, schizophrenia, major depressive disorder, bipolar disorder, attention deficit disorder, attention-deficit hyperactivity disorder, tic disorder, obsessive compulsive disorder, Tourette's syndrome, blepharospasm, post-traumatic stress disorder, panic disorder, Asperger's disorder, mild dementia of Alzheimer, dementia with Lewy bodies, Huntington's disease, personality disorders, nocturnal enuresis, and non-epileptic seizures.

As used herein, the term "neuropsychiatric disorder with deficits in learning and memory" refers to any neuropsychiatric disorders associated with learning and/or memory deficits, which can be determined by routine medical procedures. Examples include, but are not limited to, schizophrenia, depression, obsessive compulsive disorder, post-traumatic stress disorder, addiction disorders, Alzheimer's disease, frontotemporal dementia, Parkinson's disease, Duchenne muscular dystrophy, stroke, and Fragile X syndrome.

As used herein, the term "schizophrenia" refers to a psychiatric disorder that includes at least two of the following: delusions, hallucinations, disorganized speech, grossly disorganized or catatonic behavior, or negative symptoms. Patients can be diagnosed as schizophrenic using the DSMIV criteria (APA, 1994, Diagnostic and Statistical Manual of Mental Disorders (Fourth Edition), Washington, D.C.).

As used herein, the term "personality disorders" refers to mental disorders characterized by enduring maladaptive patterns of behavior, cognition, and inner experience, exhibited across many contexts and deviating markedly from those accepted by the individual's culture. These patterns develop early, are inflexible, and are associated with significant distress or disability. Personality disorders include, but not limited to, paranoid, schizoid, schizotypal, antisocial, borderline, histrionic, narcissistic, avoidant, dependent, and obsessive-compulsive personality disorder.

A "positive symptom" of schizophrenia includes delusion and hallucination, which can be measured using PANSS (Positive and Negative Syndrome Scale; see Kay et al. (1987) Schizophrenia Bulletin 13: 261-276).

A "negative symptom" of schizophrenia include affect blunting, anergia, alogia and social withdrawal, which can be measured using SANS (the Scales for the Assessment of Negative Symptoms; see Andreasen (1983) Scales for the Assessment of Negative Symptoms (SANS), Iowa City, Iowa).

A "cognitive symptom" or "cognitive dysfunction" of schizophrenia includes impairment in obtaining, organizing, and using intellectual knowledge which can be measured by the Positive and Negative Syndrome Scale-cognitive subscale (PANSS-cognitive subscale) (Lindenmayer et al. (1994) J. Nerv. Ment. Dis. 182: 631-638) or with cognitive tasks such as the Wisconsin Card Sorting Test and battery of Measurement and Treatment Research to Improve Cognition in Schizophrenia (MATRICS, "www.matrics.ucla.edu/matrics-psychometrics-frame.htm"). Deficit of learning and/or memory is a typical cognitive symptom of schizophrenia.

The terms "health food" or "health food product" refers to any kind of liquid and solid/semi-solid materials that are used for nourishing humans and animals, for improving basic behavioral functioning, hyperactivity, anxiety, depression, sensorimotor gating, pain threshold, memory and/or cognitive functioning, body weight, or for facilitating treatment of any of the target diseases noted herein. The term "nutraceutical composition" refers to compositions containing components from food sources and conferring extra health benefits in addition to the basic nutritional value found in foods.

The terms "medical food" or "medical food product" refers to a food product formulated to be consumed or administered enterally, including a food product that is usually used under the supervision of a physician for the specific dietary management of a target disease, such as those described herein. A "medical food product" composition may refer to a composition that is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management).

The details of one or more embodiments of the disclosure are set forth herein. Other features, objects, and advantages of the disclosure will be apparent from the Detailed Description, the Examples, and the Claims.

DETAILED DESCRIPTION

The present disclosure provides a composition comprising a lithium salt of an N-substituted glycine compounds and uses thereof in mitigating symptoms associated with neuropsychiatric disorders. Such lithium salts of an N-substituted glycine compound are expected to possess advantageous physical, chemical, physiologic, and/or therapeutic features as relative to the N-substituted glycine compound in a different salt form. For example, the N-substituted glycine lithium salts are expected to show advantageous properties, including improved hygroscopicity, solubility, dissolution rate, physical stability, chemical stability, bioavailability, processability, superior pharmacokinetic and/or therapeutic properties.

I. Lithium Salts of N-Substituted Glycine Compounds and Compositions Comprising Such One aspect of the present disclosure features a lithium salt of an N-substituted glycine compound. Such lithium salt of the N-substituted glycine compound can be of Formula (I), wherein $R^1$, $R^2$, or $R^3$ each are independently hydrogen, alkyl, alkenyl, alkynyl, aralkyl, carbocyclyl, aryl, or heteroaryl, or one of $R^1$, $R^2$, and $R^3$ is absent.

In some embodiments, the lithium salts of the N-substituted glycine compound are of Formula (I-A) or Formula (I-B) described herein.

In some embodiments, at least two of $R^1$, $R^2$, or $R^3$ of any of the lithium salts of N-substituted compounds each are independently hydrogen or alkyl. In some embodiments, at least two of $R^1$, $R^2$, or $R^3$ of the lithium salts of N-substituted compounds each are independently hydrogen or $C_{1-6}$ alkyl. In some embodiments, at least two of $R^1$, $R^2$, or $R^3$ each are independently hydrogen or $C_{1-3}$ alkyl (e.g., methyl, ethyl, n-propyl, isopropyl). In some embodiments, at least two of $R^1$, $R^2$, or $R^3$ each are independently hydrogen or methyl (e.g., N,N,N-trimethyl glycine, N,N-dimethyl glycine, N-methyl glycine). In some embodiments, $R^1$ and $R^2$ are methyl, and $R^3$ is absent (i.e., N,N-dimethyl glycine); or $R^1$ is methyl, $R^2$ is hydrogen, and $R^3$ is absent (i.e., N-methyl glycine).

Any of the lithium salts of N-substituted compounds as described herein may be formulated to form a pharmaceutical composition, a nutraceutical composition, a health food, or a medical food.

In some examples, the composition described herein is a pharmaceutical composition, which further comprises a pharmaceutically acceptable carrier, an excipient, or stabilizer. Remington: The Science and Practice of Pharmacy 20th Ed. (2000) Lippincott Williams and Wilkins, Ed. K. E. Hoover. Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; benzoates, sorbate and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, serine, alanine or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In other examples, the pharmaceutical composition described herein can be formulated in sustained-release format. Suitable examples of sustained-release preparations include semipermeable matrices of solid hydrophobic polymers containing tannic acid, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation, or jntrathecal or intracerebral routes.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%.

It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

In some embodiments, any of the compositions containing the lithium salt of N-substituted glycine may further comprise tannic acid as a second therapeutic agent based on the intended therapeutic uses of the composition, for example, those described herein.

In some embodiments, the compositions described herein can be a health food or a health food product, which can be any kinds of liquid and solid/semi-solid materials that are used for nourishing humans and animals, for improving basic behavioral functioning, hyperactivity, anxiety, depression, sensorimotor gating, pain threshold, memory and/or cognitive functioning, or for facilitating treatment of any of the target diseases noted herein (e.g., a neuropsychiatric disorder, including those described herein). The health food product may be a food product (e.g., tea-based beverages, juice, soft drinks, coffee, milk, jelly, cookies, cereals, chocolates, snack bars, herbal extracts, dairy products (e.g., ice cream, and yogurt)), a food/dietary supplement, or a nutraceutical formulation.

The health food product described herein, may comprise one or more edible carriers, which confer one or more of the benefits to the product as described herein. Examples of edible carriers include starch, cyclodextrin, maltodextrin, methylcellulose, carboxy methyl cellulose, xanthan gum, and aqueous solutions thereof. Other examples include solvents, dispersion media, coatings, surfactants, antioxidants, preservatives (e.g., antibacterial agents, antifungal agents), isotonic agents, absorption delaying agents, stabilizers, gels, binders, excipients, disintegration agents, lubricants, sweetening agents, flavoring agents, dyes, such like materials and combinations thereof, as would be known to one of ordinary skill in the art. In some examples, the health food products described herein may further include neuroprotective foods, such as fish oil, flax seed oil, and/or benzoate.

In some examples, the health food product is a nutraceutical composition, which refers to compositions containing components from food sources and conferring extra health benefits in addition to the basic nutritional value found in foods. A nutraceutical composition as described herein comprises the lithium salt of an N-substituted glycine compound of Formula (I) described herein and additional ingredients and supplements that promote good health and/or enhance stability and bioactivity of the lithium salts of an N-substituted glycine compound of Formula (I).

The actions of nutraceutical compositions may be fast or/and short-term or may help achieve long-term health objectives as those described herein, e.g., improving basic behavioral functioning, hyperactivity, anxiety, depression, sensorimotor gating, pain threshold, memory and/or cognitive functioning in, e.g., human subjects who have or are at risk for a neuropsychiatric disorder. The nutraceutical compositions may be contained in an edible material, for example, as a dietary supplement or a pharmaceutical formulation. As a dietary supplement, additional nutrients, such as vitamins, minerals or amino acids may be included. The composition can also be a drink or a food product, e.g., tea, soft drink, juice, milk, coffee, cookie, cereal, chocolate, and snack bar. If desired, the composition can be sweetened by adding a sweetener such as sorbitol, maltitol, hydrogenated glucose syrup and hydrogenated starch hydrolyzate, high fructose corn syrup, cane sugar, beet sugar, pectin, or sucralose.

The nutraceutical composition disclosed herein can be in the form of a solution. For example, the nutraceutical formulation can be provided in a medium, such as a buffer, a solvent, a diluent, an inert carrier, an oil, or a creme. In some examples, the formulation is present in an aqueous solution that optionally contains a non-aqueous co-solvent, such as an alcohol. The nutraceutical composition can also be in the form of powder, paste, jelly, capsule, or tablet. Lactose and corn starch are commonly used as diluents for capsules and as carriers for tablets. Lubricating agents, such as magnesium stearate, are typically added to form tablets.

The health food products may be formulated for a suitable administration route, for example, oral administration. For oral administration, the composition can take the form of, for example, tablets or capsules, prepared by conventional means with acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Also included are bars and other chewable formulations.

In some examples, the health food product can be in a liquid form and the one or more edible carriers can be a solvent or dispersion medium comprising but not limited to, ethanol, polyol (e.g., glycerol, propylene glycol, liquid polyethylene glycol), lipids (e.g., triglycerides, vegetable oils, liposomes) or combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, it will be advisable to include an isotonic agent, such as, for example, sugars, sodium chloride or combinations thereof.

Liquid preparations for oral administration can take the form of, for example, solutions, syrups or suspensions, or they can be presented as a dry product for constitution with water or other suitable vehicle before use. In one embodiment, the liquid preparations can be formulated for administration with fruit juice. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates, benzoate or sorbate).

In certain embodiments, the composition is a medical food, which may be a food product formulated to be consumed or administered enterally. Such a food product is usually used under the supervision of a physician for the specific dietary management of a target disease, such as those described herein. In some instances, such a medical food composition is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management). In some examples, a medical food composition described herein is not one of those that would be simply recommended by a physician as part of an overall diet to manage the symptoms or reduce the risk of a disease or condition.

Any of the medical food compositions described herein, comprising lithium salt of an N-substituted glycine compound of Formula (I) and at least one carrier (e.g., those described herein), can be in the form of a liquid solution; powder, bar, wafer, a suspension in an appropriate liquid or in a suitable emulsion, as detailed below. The at least one carrier, which can be either naturally-occurring or synthetic (non-naturally occurring), would confer one or more benefits to lithium salt of an N-substituted glycine compound of Formula (I) in the composition, for example, stability, bioavailability, and/or bioactivity. Any of the carriers described herein may be used for making the medical food composition. In some embodiments, the medical food composition may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents. The medical food composition may be placed in a suitable container, which may further comprise at least an additional therapeutic agent such as those described herein.

In certain embodiments, the lithium salt of an N-substituted glycine compound of Formula (I) described herein is provided in an effective amount in the pharmaceutical composition. In certain embodiments, the effective amount is a therapeutically effective amount (e.g., an amount effective for treating and/or reducing the risk for a neuropsychiatric disorder in a subject in need thereof). In certain embodiments, the neuropsychiatric disorder is a neurological disorder, e.g., Alzheimer's disease. In certain embodiments, the neuropsychiatric disorder is schizophrenia. In certain embodiments, the effective amount is a prophylactically effective amount (e.g., amount effective for preventing a neuropsychiatric disorder in a subject in need thereof).

Pharmaceutical compositions described herein can be prepared by any method known in the art of pharmacology. In general, such preparatory methods include bringing the lithium salt of an N-substituted glycine compound of Formula (I) described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the digestive tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the digestive tract, optionally, in a delayed manner. Examples of encapsulating agents which can be used include, but are not limited to, polymeric substances and waxes.

Although the descriptions of pharmaceutical compositions provided herein are mainly directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The lithium salts of an N-substituted glycine compound of Formula (I) provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

II. Methods of Treatment

Another aspect of the present invention is to provide a method for mitigating at least one symptom of neuropsychiatric disorder, comprising administering to a subject in need an effective amount of the aforementioned a lithium salt of an N-substituted glycine compound of Formula (I) or a composition comprising such.

The lithium salts of an N-substituted glycine compound of Formula (I) described herein are useful in treating and/or preventing a neuropsychiatric disorder. In some embodiments, the neuropsychiatric disorder includes schizophrenia, psychotic disorders, major depressive disorder, Alzheimer's disease, dementia, frontotemporal dementia, mild cognitive impairment, benign forgetfulness, closed head injury, an autistic spectrum disorder, Asperger's disorder, Fragile X syndrome, attention deficit disorder, attention deficit hyperactivity disorders, combined attention-deficit hyperactivity disorder and tic disorder, obsessive compulsive disorder, tic disorders, Tourette's syndrome, childhood learning disorders, premenstrual syndrome, depression, suicidal ideation and/or behavior, bipolar disorders, anxiety disorders, panic disorders, post-traumatic stress disorder, chronic pain, eating disorders, addiction disorders, personality disorders, Parkinson's disorder, Huntington's disorder, amyotrophic lateral sclerosis, nocturnal enuresis, stroke, Duchenne muscular dystrophy, blepharospasm and non-epileptic seizures.

In some embodiments, the neuropsychiatric disorder is a neuropsychiatric disorder with hyperactivity symptoms, for example, schizophrenia, bipolar disorder, attention-deficit hyperactivity disorder, obsessive compulsive disorder, Tourette's syndrome, autism spectrum disorders, Fragile X syndrome, Parkinson's disease, dementia with Lewy bodies, and senile dementia.

In some embodiments, the neuropsychiatric disorder is a neuropsychiatric disorder having sensorimotor deficit, for example, schizophrenia, major depressive disorder, bipolar disorder, attention deficit disorder, attention-deficit hyperactivity disorder, tic disorder, obsessive compulsive disorder, Tourette's syndrome, blepharospasm, post-traumatic stress disorder, panic disorder, Asperger's disorder, mild dementia of Alzheimer, dementia with Lewy bodies, Huntington's disease, personality disorders, nocturnal enuresis, and non-epileptic seizures.

In some embodiments, the neuropsychiatric disorder is a neuropsychiatric disorder with deficits in learning and memory, for example, schizophrenia, depression, obsessive compulsive disorder, post-traumatic stress disorder, addiction disorders, Alzheimer's disease, frontotemporal dementia, Parkinson's disease, Duchenne muscular dystrophy, stroke, and Fragile X syndrome.

In some embodiments, the symptom treated or mitigated is a positive symptom of schizophrenia, a negative symptom of schizophrenia, or a cognitive symptom of schizophrenia. In some embodiments, a positive symptom of schizophrenia is delusion or hallucination. In some embodiments, a negative symptom of schizophrenia includes blunting of affect, poverty of speech and thought, apathy, anhedonia, reduced social drive, loss of motivation, lack of social interest, or inattention to social or cognitive input. In some embodiments, a cognitive symptom of schizophrenia is a deficit of learning and/or memory.

The lithium salt of an N-substituted glycine compound of Formula (I) provided herein, or a composition comprising such, can be administered by a suitable route as known to those skilled in the art, including enteral (e.g., oral), parenteral, intravenous, intramuscular, intra-arterial, intramedullary, intrathecal, subcutaneous, intraventricular, transdermal, interdermal, subcutaneous, intradermal, rectal, intravaginal, intraperitoneal, topical (as by powders, ointments, creams, and/or drops). Specifically contemplated routes include oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of the lithium salt of an N-substituted glycine compound of Formula (I) comprised in the aforementioned composition required to achieve an effective amount will vary from subject to subject, depending, for example, on species, age, and general condition of a subject, severity of the side effects or disorder, identity of the particular lithium salt of an N-substituted glycine compound of Formula (I), mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of the lithium salt of an N-substituted glycine compound of Formula (I) described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, one dose every week, one dose every other week, one dose monthly or one dose every other month. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of the lithium salt of an N-substituted glycine compound of Formula (I) described herein. In certain embodiments, a dose described herein includes independently between 3 mg and 10 mg, inclusive, of the lithium salt of an N-substituted glycine compound of Formula (I) described herein. In certain embodiments, a dose described herein includes independently between 10 mg and 30 mg, inclusive, of the lithium salt of an N-substituted glycine compound of Formula (I) described herein. In certain embodiments, a dose described herein includes independently between 30 mg and 100 mg, inclusive, of the lithium salt of an N-substituted glycine compound of Formula (I) described herein. In certain embodiments, a dose described herein includes independently between 100 mg and 300 mg, inclusive, of the lithium salt of an N-substituted glycine compound of Formula (I) as described herein. In certain embodiments, a dose described herein includes independently between 300 mg and 1000 mg, inclusive, of the lithium salt of an N-substituted glycine compound of Formula (I) described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

III. Combined Treatment

The lithium salt of an N-substituted glycine compound of Formula (I), as described herein, can be administered in combination with one or more additional pharmaceutical agents (e.g., therapeutically and/or prophylactically active agents) useful in treating and/or reducing the risk for a neuropsychiatric disorder. The additional pharmaceutical agents may improve the activity (e.g., activity (e.g., potency and/or efficacy) of the lithium salt of the N-substituted glycine compound in treating and/or reducing the risk for a neuropsychiatric disorder in a subject in need thereof), improve bioavailability, improve safety, reduce drug resistance, reduce and/or modify metabolism, inhibit excretion, and/or modify distribution of the lithium salt of the N-substituted glycine compound in a subject, biological sample, tissue, or cell. It will also be appreciated that the therapy employed may achieve a desired effect for the same disorder, and/or it may achieve different effects. In certain embodiments, the lithium salt of an N-substituted glycine compound of Formula (I) described herein and the additional pharmaceutical agent show a synergistic effect that is absent in a treatment involving one of the lithium salt of an N-substituted glycine compound of Formula (I) and the additional pharmaceutical agent, but not both.

The lithium salt of an N-substituted glycine compound of Formula (I) can be administered concurrently with, prior to, currently with, or subsequent to one or more additional pharmaceutical agents, which may be useful as, e.g., combination therapies in treating and/or reducing the risk for a neuropsychiatric disorder in a subject. In some examples, the lithium salt of the N-substituted glycine compound and the additional pharmaceutical agent(s) are formulated in one composition. In other examples, the lithium salt of the N-substituted glycine compound and the additional pharmaceutical agent(s) are formulated in separate compositions.

Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, antibodies, small molecules linked to proteins such as antibodies, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating and/or reducing the risk for a neuropsychiatric disorder in a subject. In certain embodiments, the additional pharmaceutical agent is a pharmaceutical agent approved by a regulatory agency (e.g., the US FDA) for treating and/or reducing the risk for a neuropsychiatric disorder in a subject. Each additional pharmaceutical agent may be administered at a dose and/or on a time schedule determined for that pharmaceutical agent. The additional pharmaceutical agents may also be administered together with each other and/or with the composition comprising the lithium salt of an N-substituted glycine compound of Formula (I) described herein in a single dose or administered separately in different doses. The particular combination to employ in a regimen will take into account compatibility of the lithium salt of an N-substituted glycine compound of Formula (I) described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is selected from agents for treating and/or reducing the risk for a neuropsychiatric disorder, or combinations thereof. In certain embodiments, the pharmaceutical compositions comprising the lithium salts of an N-substituted glycine compound of Formula (I) described herein can be administered in combination with a therapy for treating and/or reducing the risk for a neuropsychiatric disorder.

In certain embodiments, the additional pharmaceutical agent is an agent for treating and/or reducing the risk for a neuropsychiatric disorder can be an antipsychotic, an antidepressant, a mood stabilizer, an anxiolytic, a psychostimulant and an agent for treating attention deficit hyperactivity disorder (ADHD), or an agent for treating Alzheimer's disease (AD).

Examples of antipsychotics include, but not limited to, butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupentixol, thiothixene, zuclopenthixol, clozapine, olanzapine, risperidone, quetiapine, ziprasidone, amisulpride, asenapine, paliperidone, aripiprazole, cannabidiol, LY2140023, droperidol, pimozide, butaperazine, carphenazine, remoxipride, piperacetazine, sulpiride, acamprosate, tannic acid, and tetrabenazine.

The antidepressants can be monoamine oxidase inhibitors (MAOIs), tricyclic antidepressants (TCAs), tetracyclic antidepressants (TeCAs), selective serotonin reuptake inhibitors (SSRIs), noradrenergic and specific serotonergic antidepressants (NASSAs), norepinephrine (noradrenaline) reuptake inhibitors, norepinephrine-dopamine reuptake inhibitors, or serotonin-norepinephrine reuptake inhibitors (SNRIs). Examples of the antidepressants include, but not limited to, fluoxetine, paroxetine, escitalopram, citalopram, sertraline, fluvoxamine, venlafaxine, milnacipran, duloxetine, mirtazapine, mianserin, reboxetine, bupropion, amitriptyline, nortriptyline, protriptyline, desipramine, trimipramine, amoxapine, bupropion, clomipramine, desipramine, doxepin, isocarboxazid, tranylcypromine, trazodone, nefazodone, phenelzine, lamatrogine, lithium, topiramate, gabapentin, carbamazepine, oxcarbazepine, valproate, maprotiline, brofaromine, gepirone, moclobemide, isoniazid, and iproniazid.

The psychostimulant or the agent for treating attention deficit hyperactivity disorder (ADHD) can be methylphenidate, dextro-threo-methylphenidate, isopropylphenidate, cocaine, amphetamine, methamphetamine, dextroamphetamine, 3,4-methylenedioxymethamphetamine, pemoline, phenmetrazine, diethylpropion, chlorphentermine, pipradol, p-hydroxymorphedrine, fenfluramine, 1-(2,5-dimethoxy-4-methylphenyl)-2-aminopropane, bupropion, statins, modafinil, arecoline, dexmethylphenidate, lisdexamfetamine dimesylate, mixed salts amphetamine, atomoxetine, clonidine hydrochloride, guanfacine hydrochloride, and arecoline.

The mood stabilizers can be lithium, lamotrigine, carbamazepine, topiramate, zolpidem, carbamazepine, and valproate.

The anxiolytics can be diazepam, alprazolam, triazolam, indiplon, zaleplon, bromazepam, oxazepam, buspirone, hydroxyzine, mecloqualone, medetomidine, metomidate, adinazolam, chlordiazepoxide, clobenzepam, flurazepam, lorazepam, clonazepam, loprazolam, midazolam, alpidem, alseroxlon, amphenidone, azacyclonol, bromisovalum, chlorazepate, calcium N-carboamoylaspartate, captodiamine, capuride, carbcloral, carbromal, chloral betaine, enciprazine, flesinoxan, ipsapiraone, ipsapirone, lesopitron, loxapine, methaqualone, methprylon, propanolol, tandospirone, trazadone, zopiclone, and zolpidem.

The agent for treating Alzheimer's disease (AD) can be donepezil, rivastigmine, galantamine, memantine, selfotel, midafotel, tacrine, selegiline, and vitamin E.

IV. Kits for Treatment

Also encompassed by the present disclosure are kits for use in treating any of the target disorders described herein. The kits provided herein may comprise a lithium salt of an N-substituted glycine compound of Formula (I) described herein, or a composition comprising such. Optionally, the kit may further comprise one or more additional pharmaceutical agents as described herein.

Any of the kits described herein may comprise one or more containers (e.g., a vial, ampule, bottle, syringe, and/or dispenser package, or other suitable container), in which the active ingredients noted herein are placed. In some embodiments, provided kits may optionally further include an additional container comprising a pharmaceutical excipient for dilution or suspension of a pharmaceutical composition comprising the lithium salt of an N-substituted glycine compound of Formula (I) described herein, and optionally the additional pharmaceutical agents. In some embodiments, the pharmaceutical composition comprising the lithium salt of an N-substituted glycine compound of Formula (I) described herein provided in the one or more containers are combined to form one unit dosage form.

In certain embodiments, a kit described herein further includes instructions for using the composition comprising a lithium salt of an N-substituted glycine compound of Formula (I) included in the kit. A kit described herein may also include information as required by a regulatory agency such as the U.S. Food and Drug Administration (FDA). In certain embodiments, the information included in the kits is prescribing information. In certain embodiments, the kits and instructions provide for treating and/or reducing the risk for a neuropsychiatric. A kit described herein may include one or more additional pharmaceutical agents described herein as a separate composition.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Synthesis and Preparation of Lithium N-Methylglycine

A solution of 49.1 g of N-methylglycine in 200 mL of water was cooled to 0° C. with stirring, then a solution of 23.1 g of LiOH in 50 mL of water was added. The mixture was kept stirring at 0 to 25° C. for 3 h, then concentrated in vacuo to remove water and to afford the lithium N-methylglycine salt, which was re-crystallized with isopropyl alcohol to give a crystalline form of lithium N-methylglycine (49.6 g, yield 94%) which was used in the following example.

Example 2: Effects of Lithium N-Methylglycine on Behavior of MK801-Treated Mice

All C57BL/6J male mice were purchased from Laboratory Animal Center of the College of Medicine of National Taiwan University. The mice were group housed (3-5 mice per cage) with food and water available ad libitum in polysulfone ventilated cages (Alternative Design, AR, USA) in the animal rooms of the Psychology Department of National Taiwan University. The colony was maintained on a 12/12-h light/dark cycle at the temperature of 22±2° C. and all behavioral studies were performed during dark cycle. All animals used in this study were adult mice (at least 2.5 months of age). All animal procedures were performed according to the protocols approved by Animal Care and Use Committee of National Taiwan University.

The mice were randomly assigned into six groups:
Group 1: PBS+Saline (n=9) (control group);
Group 2: PBS+MK801 (n=9) (MK801 group);
Group 3: N-methylglycine_278 mg/kg+MK801 (n=7);
Group 4: N-methylglycine_927 mg/kg+MK801 (n=7);
Group 5: lithium N-methylglycine_300 mg/kg+MK801 (n=8);
Group 6: lithium N-methylglycine_1000 mg/kg+MK801 (n=8).

MK801, also known as dizocilpine, is an antagonist of NMDA receptor. Mice in Groups 2-6 were received an acute administration of MK-801 (a NMDA receptor antagonist, dissolved in normal saline, 0.1 or 0.2 mg/kg, i.p.) 20 min prior to behavioral tests. Mice in Groups 3-6 were received an oral gavage of N-methylglycine or lithium N-methylglycine, respectively (dissolved in PBS) 15 min prior to MK801 administration. The high and low molarities of lithium N-methylglycine (300 mg/kg and 1000 mg/kg) were equal to those of N-methylglycine (278 mg/kg and 927 mg/kg), respectively.

Two cohorts (48 mice) of mice were used in the present study, the cohort 1 (48 mice) were sequentially tested with open field (for MK801-induced hyper-locomotion) and pre-pulse inhibition (for sensor-motor gap function) tasks. The mice in cohort 2 (34 mice) were sequentially tested with Barnes maze (spatial learning and memory) task.

Figure 1:
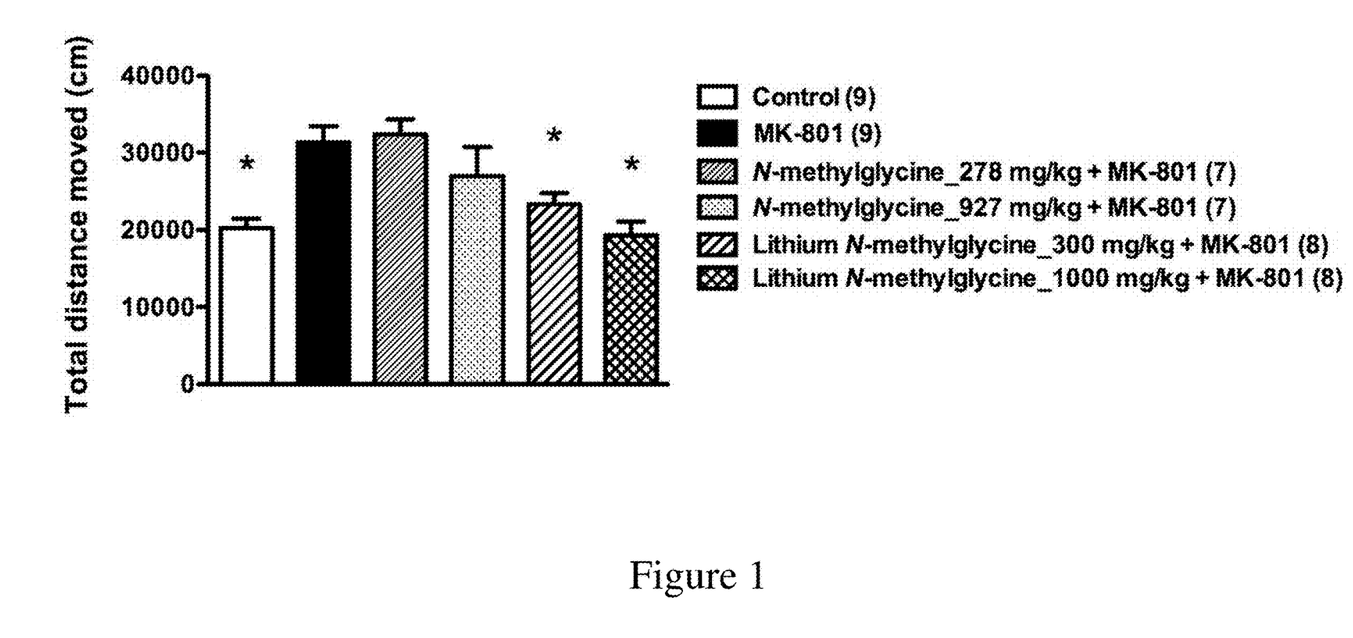
FIG. 1 shows the total distance traveled by mice within the following groups in the open-field task described in Examples: control (n=9), MK801 (n=9), N-methylglycine_278 mg/kg+MK801 (n=7), N-methylglycine_927 mg/kg+MK801 (n=7), Lithium N-methylglycine_300 mg/kg+MK801 (n=8) and lithium N-methylglycine_1000 mg/kg+MK801 (n=8).

Lithium N-Methylglycine Decreased MK801-Induced Hyper-Locomotion in Mouse Open Field Task The open field task is a common measure of novel environment-induced exploratory behavior and general activity in both mice and rats. In the present study, the mice were placed in a Plexiglas cage (37.5 cm×21.5 cm×18 cm) under 50-65 lux light intensity, and their spontaneous locomotor activity was measured for 60 minutes using the EthoVision video tracking system (Noldus Information Technology, the Netherlands). The travel distance of each mouse was measured as an index of locomotion activity. The results are shown in FIG. 1.

Compared to the control group, MK-801 induced the hyper-locomotion in the open field test. Animal models involving MK-801 induced hyperactivity are commonly used in studying various neuropsychiatric disorders, and developing an analysis of conditions including, but not limited to, schizophrenia, bipolar disorder, attention-deficit hyperactivity disorder, obsessive compulsive disorder, Tourette's syndrome, autism spectrum disorders, Fragile X syndrome, Parkinson's disease, dementia with Lewy bodies, and senile dementia (see Rubia et al., 2010; Sheppard and Bradshaw, 1999; Bent et al., 2014; Powell and Miyakawa, 2006; Nestler and Hyman, 2010; Bubem'kova'-Valesova et al., 2008; Gobira et al., 2013; Lai et al., 2014; Maio et al., 2014; Sontag et al., 2010; Ding et al., 2014; Walitza et al., 2007; Finestone et al., 1982; Golimstok et al., 2011).

High dose of N-methylglycine and both dosages of lithium N-methylglycine ameliorated the MK-801 induced hyper-locomotion activity. Dose-dependent effect could be observed in lithium N-methylglycine+MK-801 groups. Hyper-locomotion is deemed as a typical positive symptom of schizophrenia, and this result indicates that a high dose of N-methylglycine (927 mg/kg) is marginally effective while both dosages of lithium N-methylglycine (300 mg/kg and 1000 mg/kg) are effective for treatment of positive symptoms. Therefore, lithium N-methylglycine is much more effective than N-methylglycine in reducing hyperactivity induced by MK-801.

Lithium N-Methylglycine Alleviated MK801-Induced Sensor-Motor Function Impairment in Pre-Pulse Inhibition Task Pre-attentive processes tend to be automatic and rapid and to operate outside of conscious awareness, whereas deliberate attention processes have limited resources, are effortful, and operate more slowly. A common measure of pre-attentive processing is pre-pulse inhibition. This paradigm has been commonly examined in mouse models of several mental illnesses, including, but not limited to, schizophrenia, major depressive disorder, bipolar disorder, attention deficit disorder, attention-deficit hyperactivity disorder, tic disorder, obsessive compulsive disorder, Tourette's syndrome, blepharospasm, post-traumatic stress disorder, panic disorder, Asperger's disorder, mild dementia of Alzheimer, dementia with Lewy bodies, Huntington's disease, personality disorders, nocturnal enuresis, and non-epileptic seizures (see McAlonan et al., 2002; Braff et al., 2001; Giakoumaki et al., 2007; Ueki et al., 2006; Perriol et al., 2005; Ludewig et al., 2002; Castellanos et al., 1996; Cadenhead et al., 2000; Matsuo et al., 2017; Lai et al., 2014) because the deficit manifests in a similar manner to the human symptom.

Figure 2:
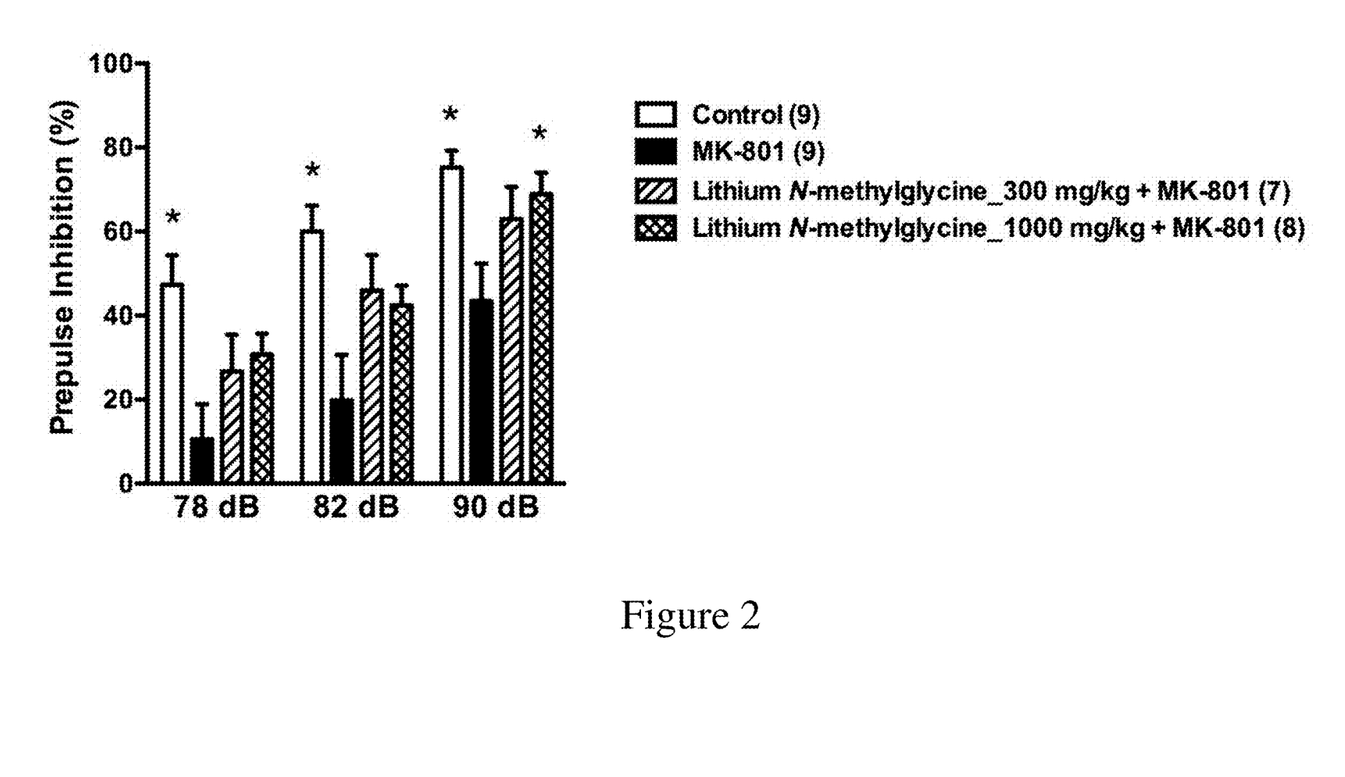
FIG. 2 shows the percentage of pre-pulse inhibition shown by mice within the following groups in the pre-pulse inhibition task described in Example 2B: control (n=9), MK801 (n=9), Lithium N-methylglycine_300 mg/kg+MK801 (n=7) and lithium N-methylglycine_1000 mg/kg+MK801 (n=8) at 78 dB, 82 dB and 90 dB of prepulse.

Pre-pulse inhibition was used as an index of sensorimotor gating function using SR-LAB startle apparatus (San Diego Instruments, San Diego, Calif., USA). Under a 72 dB background noise, each session composed of 5 minutes of accumulation period followed by 64 trials in four blocks. The pulse alone (PA) trial was a 40 ms, 120 dB white noise burst. In the pre-pulse (pp)+pulse trials, a 20 ms white noise pre-pulse stimuli of 78 dB (pp6), 82 dB (pp10) or 90 dB (pp18) was presented 100 ms before a 40 ms 120 dB pulse. The non-stimulus (NS) trials presented the background noise only. The initial and the last blocks are composed of six PA trials respectively. Two middle blocks consist of PA, pp+pulse, and NS trials. These trials were presented pseudo-randomly and separated by intertribal interval of 15 s on average (varying between 10 to 20 s). The percentage of pre-pulse inhibition was evaluated by the following formula: % PPI=100×[(PA score)−(pp-P score)]/(PA score), where the PA score was the average of the PA value in the middle blocks. The results are shown in FIG. 2.

Compared to the control group, MK-801 induced the sensorimotor gating function deficit in the pre-pulse inhibition test. The pre-pulse inhibition was alleviated by lithium N-methylglycine treatments after MK-801 injection, especially at high intensity of pre-pulse (90 dB). The results obtained from this study show that lithium N-methylglycine is effective for mitigating deficits in prepulse inhibition models of CNS disorders.

Figure 3:
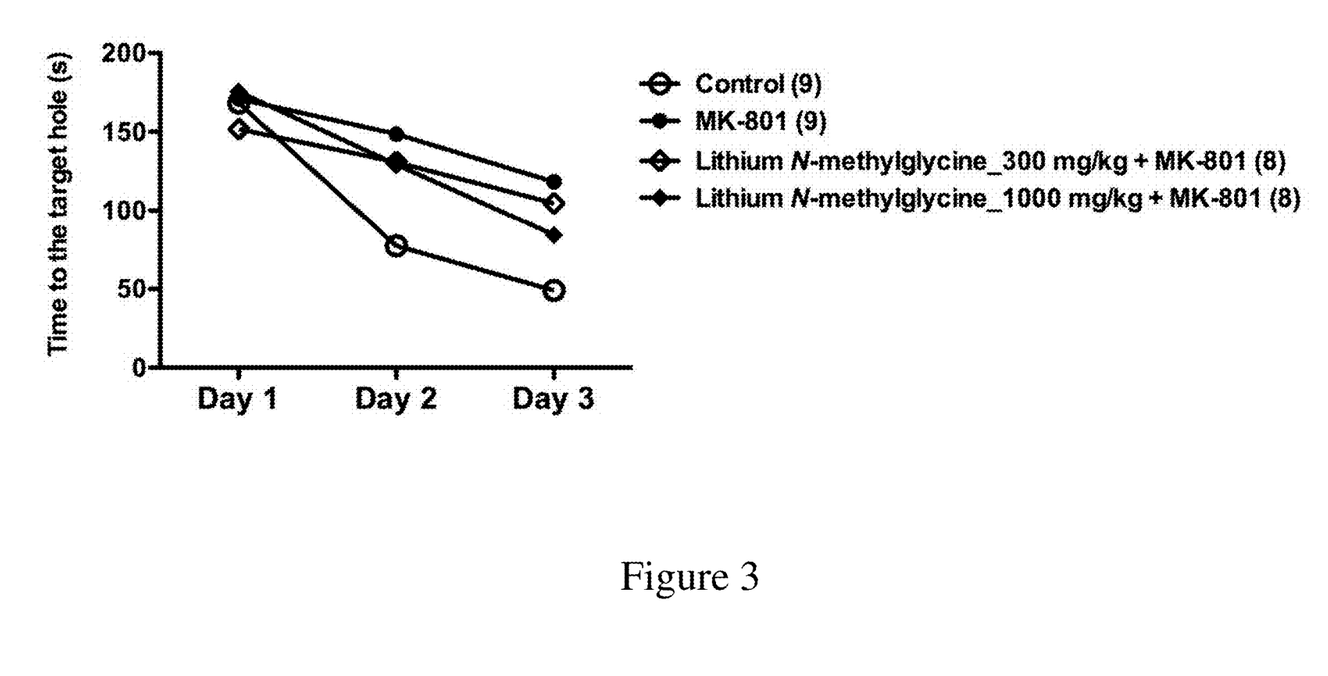
FIG. 3 shows the amount of time that the mice of the following groups took to reach the target hole in the training trials of Barnes maze task described in Example 2C: control (n=9), MK801 (n=9), Lithium N-methylglycine_300 mg/kg+MK801 (n=8) and lithium N-methylglycine_1000 mg/kg+MK801 (n=8).
Figure 4:
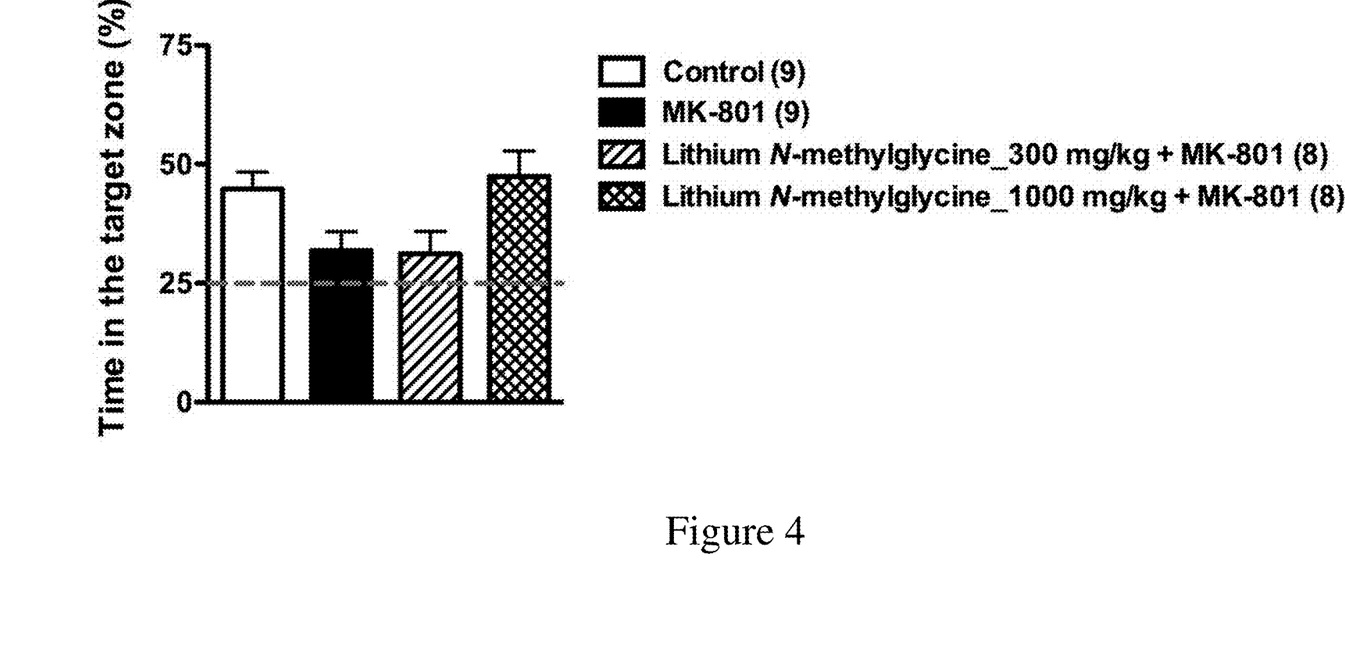
FIG. 4 shows the amount of time the mice of the following groups spent in the target zone during the probe tests of Barnes maze task described in Example 2C: control (n=9), MK801 (n=9), Lithium N-methylglycine_300 mg/kg+MK801 (n=8) and lithium N-methylglycine_1000 mg/kg+MK801 (n=8).

Lithium N-Methylglycine Alleviated MK801-Induced Spatial Learning & Memory Deficits in Barnes Maze Task Mice were tested in a Barnes maze to examine spatial learning and memory as described previously (Barnes, 1979). This Barnes maze paradigm has been commonly examined in mouse models of CNS disorders, including, but not limited to, schizophrenia, depression, obsessive compulsive disorder, post-traumatic stress disorder, addiction disorders, Alzheimer's disease, frontotemporal dementia, Parkinson's disease, Duchenne muscular dystrophy, stroke, and Fragile X syndrome (see Cook et al., 2014; Götz and Ittner, 2008; Hendriksen and Vles, 2008; Conklin et al., 2000; Song et al., 2006; Lai et al., 2014; Vasterling et al., 2002; Hyman, 2005; Schaar et al., 2010; Santos et al., 2014; Zhu et al., 2007; Deckersbach et al., 2000). The testing apparatus was an elevated (50 cm above the floor) circular Plexiglas plate (100 cm in diameter) with 20 holes (7 cm in diameter, 7 cm between holes) evenly spaced around the perimeter. Mice were trained on the plate to identify an escape box (25×8×6 cm) hidden behind the target hole, which was designated as an analog to the hidden platform in the Morris water maze task. The location of the target hole was selected for a given mouse but randomized across mice. Mice were initially placed in the center of the plate covered by an opaque cylinder, and the cylinder was removed 10 s after the beginning of the trial with both an aversive tone (440 Hz, 85 dB) and light (100 lux) switched on. Mice were trained to locate the target hole according to surrounding visual cues and escape from the aversive tone for three training trials per day over 3 consecutive days. The spatial memory was measured by the "probe test." All the training trials and the probe tests were videotaped for 3 min, and then the escape latency for the training trials and the percentage of time in different quadrants (target, left, right, and opposite) during the probe test were analyzed. The time taken by the mice to reach the target hole in the training trials is shown in FIG. 3, and the percentage of time they spent in the target zone during the probe tests is shown in FIG. 4.

Compared to the control group, mice treated with MK-801 (dissolved in normal saline, 0.2 mg/kg, i.p.) showed poor learning ability and memory deficit by the Barnes maze task. In the learning phase, high dosage of lithium N-methylglycine (1000 mg/kg) enhances the learning after MK-801 induced learning deficit. In the memory phase, the high dose of lithium N-methylglycine treatment completely ameliorated the memory deficit while N-methylglycine is not effective. Therefore, lithium N-methylglycine treatment is much superior as compared with N-methylglycine to recover memory deficit induced by the MK-801 treatment.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A composition comprising a therapeutically effective or prophylactically effective amount of a lithium salt of N-methylglycine and a carrier.

2. The composition of claim 1, which is a pharmaceutical composition, a nutraceutical composition, a health food, or a medical food.

3. The composition of claim 1, wherein the composition is a dosage form containing 30 mg to 10 g of the lithium salt of N-methylglycine.

4. The composition of claim 3, wherein the dosage form contains 100 mg to 10 g of the lithium salt of N-methylglycine.

5. The composition of claim 4, wherein the dosage form contains 300 mg to 10 g of the lithium salt of N-methylglycine.

6. A method for mitigating a symptom of a neuropsychiatric disorder, comprising administering to a subject in need thereof an effective amount of a lithium salt of N-methylglycine or a composition comprising the lithium salt.

7. The method of claim 6, wherein the neuropsychiatric disorder is a neuropsychiatric disorder with hyperactivity symptoms.

8. The method of claim 7, wherein the neuropsychiatric disorder is selected from the group consisting of schizophrenia, bipolar disorder, attention-deficit hyperactivity disorder, obsessive compulsive disorder, Tourette's syndrome, autism spectrum disorders, Fragile X syndrome, Parkinson's disease, dementia with Lewy bodies, and senile dementia.

9. The method of claim 6, wherein the neuropsychiatric disorder is a neuropsychiatric disorder having sensorimotor deficit.

10. The method of claim 9, wherein the neuropsychiatric disorder is selected from the group consisting of schizophrenia, major depressive disorder, bipolar disorder, attention deficit disorder, attention-deficit hyperactivity disorder, tic disorder, obsessive compulsive disorder, Tourette's syndrome, blepharospasm, post-traumatic stress disorder, panic disorder, Asperger's disorder, mild dementia of Alzheimer, dementia with Lewy bodies, Huntington's disease, personality disorders, nocturnal enuresis, and non-epileptic seizures.

11. The method of claim 6, wherein the neuropsychiatric disorder is a neuropsychiatric disorder with a deficit in learning and memory.

12. The method of claim 11, wherein the neuropsychiatric disorder is selected from the group consisting of schizophrenia, depression, obsessive compulsive disorder, post-traumatic stress disorder, addiction disorders, Alzheimer's disease, frontotemporal dementia, Parkinson's disease, Duchenne muscular dystrophy, stroke, and Fragile X syndrome.

13. The method of claim 6, wherein the subject is treated by an additional pharmaceutical agent for the neuropsychiatric disorder.

14. The method of claim 13, wherein the additional pharmaceutical agent is selected from the group consisting of an antipsychotic, an antidepressant, a mood stabilizer, an anxiolytic, or a psychostimulant.

15. The method of claim 14, wherein the additional pharmaceutical agent is an antipsychotic selected from the group consisting of butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupentixol, thiothixene, zuclopenthixol, clozapine, olanzapine, risperidone, quetiapine, ziprasidone, amisulpride, asenapine, paliperidone, aripiprazole, cannabidiol, LY2140023, droperidol, pimozide, butaperazine, carphenazine, remoxipride, piperacetazine, sulpiride, acamprosate, tannic acid, and tetrabenazine.

16. The method of claim 14, wherein the additional pharmaceutical agent is an antidepressant selected from the group consisting of monoamine oxidase inhibitors (MAOIs), tricyclic antidepressants (TCAs), tetracyclic antidepressants (TeCAs), selective serotonin reuptake inhibitors (SSRIs), noradrenergic and specific serotonergic antidepressants (NASSAs), norepinephrine (noradrenaline) reuptake inhibitors, norepinephrine-dopamine reuptake inhibitors, and serotonin-norepinephrine reuptake inhibitors (SNRIs).

17. The method of claim 14, wherein the additional pharmaceutical agent is an antidepressant selected from the group consisting of fluoxetine, paroxetine, escitalopram, citalopram, sertraline, fluvoxamine, venlafaxine, milnacipran, duloxetine, mirtazapine, mianserin, reboxetine, bupropion, amitriptyline, nortriptyline, protriptyline, desipramine, trimipramine, amoxapine, bupropion, clomipramine, desipramine, doxepin, isocarboxazid, tranylcypromine, trazodone, nefazodone, phenelzine, lamatrogine, lithium, topiramate, gabapentin, carbamazepine, oxcarbazepine, valproate, maprotiline, brofaromine, gepirone, moclobemide, isoniazid, and iproniazid.

18. The method of claim 14, wherein the additional pharmaceutical agent is a psychostimulant selected from the group consisting of methylphenidate, dextro-threo-methylphenidate, isopropylphenidate, cocaine, amphetamine, methamphetamine, dextroamphetamine, 3,4-methylenedioxymethamphetamine, pemoline, phenmetrazine, diethylpropion, chlorphentermine, pipradol, p-hydroxymorphedrine, fenfluramine, 1-(2,5-dimethoxy-4-methylphenyl)-2-aminopropane, bupropion, statins, modafinil, arecoline, dexmethylphenidate, lisdexamfetamine dimesylate, mixed salts amphetamine, atomoxetine, clonidine hydrochloride, guanfacine hydrochloride, and arecoline.

19. The method of claim 14, wherein the additional pharmaceutical agent is a mood stabilizer selected from the group consisting of lithium, lamotrigine, carbamazepine, topiramate, zolpidem, carbamazepine, and valproate.

20. The method of claim 14, wherein the additional pharmaceutical agent is an anxiolytic selected from the group consisting of diazepam, alprazolam, triazolam, indiplon, zaleplon, bromazepam, oxazepam, buspirone, hydroxyzine, mecloqualone, medetomidine, metomidate, adinazolam, chlordiazepoxide, clobenzepam, flurazepam, lorazepam, clonazepam, loprazolam, midazolam, alpidem, alseroxlon, amphenidone, azacyclonol, bromisovalum, chlorazepate, calcium N-carboamoylaspartate, captodiamine, capuride, carbcloral, carbromal, chloral betaine, encipra-zine, flesinoxan, ipsapiraone, ipsapirone, lesopitron, loxap-ine, methaqualone, methprylon, propanolol, tandospirone, trazadone, zopiclone, and zolpidem.

21. The method of claim 13, wherein the disorder is Alzheimer's disease (AD) and the additional pharmaceutical agent is selected from the group consisting of donepezil, rivastigmine, galantamine, memantine, selfotel, midafotel, tacrine, selegiline, and vitamin E.

22. The method of claim 13, wherein the additional pharmaceutical agent is administered prior to, concurrently with, or subsequent to the administration of the lithium salt of N-methylglycine.

* * * * *

UNITED STATES PATENT AND TRADEMARK OFFICE
CERTIFICATE OF CORRECTION

PATENT NO. : 10,226,442 B2
APPLICATION NO. : 15/646034
DATED : March 12, 2019
INVENTOR(S) : Guochuan Emil Tsai et al.

It is certified that error appears in the above-identified patent and that said Letters Patent is hereby corrected as shown below:

On the Title Page

Item (71) SyneuRx International (Taiwan) Corp., New Taipei (TW) should be -- SyneuRx International (Taiwan) Corp., New Taipei City (TW) --

Item (72) Guochuan Emil Tsai, Pasadena, CA (US); Ching-Hsun Huang, Taipei (TW); Han-Yi Hsieh, New Taipei (TW); Jing-Jia Huang, New Taipei (TW); Ching-Cheng Wang, New Taipei (TW) should be -- Guochuan Emil Tsai, Pasadena, CA (US); Ching-Hsun Huang, Taipei (TW); Han-Yi Hsieh, New Taipei City (TW); Jing-Jia Huang, New Taipei City (TW); Ching-Cheng Wang, New Taipei City (TW) --

Item (73) SyneuRx International (Taiwan) Corp., New Taipei (TW) should be -- SyneuRx International (Taiwan) Corp., New Taipei City (TW) --

Signed and Sealed this
Twenty-first Day of May, 2019

Andrei Iancu
*Director of the United States Patent and Trademark Office*